(12) United States Patent
Pyles et al.

(10) Patent No.: US 12,141,876 B2
(45) Date of Patent: Nov. 12, 2024

(54) EXERCISE APPARATUS WITH EXERCISE USE VERIFICATION FUNCTION AND VERIFYING METHOD

(71) Applicant: Johnson Health Tech. Co., Ltd., Taichung (TW)

(72) Inventors: Nathan Pyles, Lake Mills, WI (US); Hung-Mao Liao, Taichung (TW); Joe Chen, Taichung (TW)

(73) Assignee: Johnson Health Tech Co., Ltd., Taichung (TW)

( * ) Notice: Subject to any disclaimer, the term of this patent is extended or adjusted under 35 U.S.C. 154(b) by 442 days.

(21) Appl. No.: 17/581,967

(22) Filed: Jan. 23, 2022

(65) Prior Publication Data

US 2022/0148095 A1    May 12, 2022

Related U.S. Application Data

(63) Continuation-in-part of application No. 17/210,031, filed on Mar. 23, 2021, now Pat. No. 11,995,725,
(Continued)

(51) Int. Cl.
*G06Q 40/08* (2012.01)
*A63B 22/02* (2006.01)
(Continued)

(52) U.S. Cl.
CPC ......... *G06Q 40/08* (2013.01); *A63B 22/0235* (2013.01); *A63B 24/0062* (2013.01);
(Continued)

(58) Field of Classification Search
CPC ............... G06Q 40/08; A63B 22/0235; A63B 24/0062; A63B 24/0087; A63B 22/025; A63B 22/04; A63B 2024/0093; A63B 2024/0096; A63B 2220/13; A63B 2220/20; A63B 2220/30; A63B 2220/56; A63B 2220/62; A63B 2220/805; A63B 2225/20;
(Continued)

(56) References Cited

U.S. PATENT DOCUMENTS 5,209,710 A * 5/1993 Shimizu ................. A63B 22/02
                                                482/54
5,290,205 A * 3/1994 Densmore ............ A63B 22/025
                                                482/901

(Continued)

*Primary Examiner* — Sundhara M Ganesan

(57) ABSTRACT

A motorized treadmill provided for allowing a user to perform a programed workout. The motorized treadmill includes a base, an endless belt movable relative to the base for allowing a user to exercise thereon, a motor coupled to the endless belt for driving the endless belt to rotate, a signal receiver, and a controller in communication with the motor and the signal receiver. The signal receiver is configured to receive a weight training signal when the user performs the programed workout with free weight equipment. The controller is configured to transmit validated exercise use data when the user is engaging the endless belt. When the signal receiver receives the weight training signal from the free weight equipment, the controller will determine that the user is not engaging the endless belt and stops transmitting the validated exercise use data.

20 Claims, 13 Drawing Sheets

Related U.S. Application Data which is a continuation-in-part of application No. 17/026,847, filed on Sep. 21, 2020, now Pat. No. 11,663,673, which is a continuation of application No. 16/043,925, filed on Jul. 24, 2018, now Pat. No. 10,796,375, which is a continuation of application No. 14/983,171, filed on Dec. 29, 2015, now Pat. No. 10,032,227.

(60) Provisional application No. 62/098,309, filed on Dec. 30, 2014.

(51) Int. Cl.
*A63B 24/00* (2006.01)
*G16H 20/30* (2018.01)
*A63B 22/04* (2006.01)

(52) U.S. Cl.
CPC ......... *A63B 24/0087* (2013.01); *G16H 20/30* (2018.01); *A63B 22/025* (2015.10); *A63B 22/04* (2013.01); *A63B 2024/0093* (2013.01); *A63B 2024/0096* (2013.01); *A63B 2220/13* (2013.01); *A63B 2220/20* (2013.01); *A63B 2220/30* (2013.01); *A63B 2220/56* (2013.01); *A63B 2220/62* (2013.01); *A63B 2220/805* (2013.01); *A63B 2225/20* (2013.01); *A63B 2225/50* (2013.01); *A63B 2230/50* (2013.01); *A63B 2230/505* (2013.01)

(58) Field of Classification Search
CPC ............ A63B 2225/50; A63B 2230/50; A63B 2230/505; A63B 21/072; A63B 21/0726; G16H 20/30
See application file for complete search history.

(56) References Cited

U.S. PATENT DOCUMENTS

| | | | | |
|---|---|---|---|---|
| 5,747,955 | A * | 5/1998 | Rotunda | A63B 22/025 318/434 |
| 6,050,924 | A * | 4/2000 | Shea | A63B 24/0062 482/901 |
| 6,055,359 | A * | 4/2000 | Gillett | H02P 7/29 318/432 |
| 6,416,444 | B1 * | 7/2002 | Lim | A63B 24/00 482/54 |
| 6,575,878 | B1 * | 6/2003 | Choy | A63B 22/0235 482/8 |
| 7,048,676 | B1 * | 5/2006 | Wu | A63B 22/0235 482/54 |
| 7,141,006 | B1 * | 11/2006 | Chen | A63B 22/02 482/7 |
| 9,039,580 | B1 * | 5/2015 | Bayerlein | A63B 21/157 482/54 |
| 9,186,552 | B1 * | 11/2015 | Deal | A63B 71/0619 |
| 9,785,827 | B1 * | 10/2017 | Ray | A63B 24/0087 |
| 2002/0055419 | A1 * | 5/2002 | Hinnebusch | A63B 24/0084 482/8 |
| 2004/0133081 | A1 * | 7/2004 | Teller | A61B 5/4884 600/595 |
| 2006/0205566 | A1 * | 9/2006 | Watterson | H04L 12/40045 482/902 |
| 2006/0276306 | A1 * | 12/2006 | Pan | A63B 22/02 482/54 |
| 2008/0032870 | A1 * | 2/2008 | Wu | A63B 22/0235 482/8 |
| 2008/0204225 | A1 * | 8/2008 | Kitchen | A63B 21/072 340/539.22 |
| 2009/0176629 | A1 * | 7/2009 | Yi | A63B 22/025 482/54 |
| 2010/0016678 | A1 * | 1/2010 | Beck | A61B 5/222 600/300 |
| 2011/0059825 | A1 * | 3/2011 | Mcgown | A63B 24/0062 702/176 |
| 2011/0191158 | A1 * | 8/2011 | Kateraas | G06Q 30/02 705/14.27 |
| 2012/0040799 | A1 * | 2/2012 | Jaquish | A63B 23/0355 482/9 |
| 2012/0071770 | A1 * | 3/2012 | Grey | A61B 5/389 600/508 |
| 2012/0237911 | A1 * | 9/2012 | Watterson | G10L 15/26 482/4 |
| 2012/0296455 | A1 * | 11/2012 | Ohnemus | G16H 10/60 700/91 |
| 2013/0035215 | A1 * | 2/2013 | Ashby | A63B 22/0242 482/54 |
| 2013/0143718 | A1 * | 6/2013 | Pani | A63B 21/4035 482/8 |
| 2013/0211562 | A1 * | 8/2013 | Winter | A63B 24/0062 700/91 |
| 2013/0274066 | A1 * | 10/2013 | Ashby | A63B 24/0062 482/4 |
| 2013/0330694 | A1 * | 12/2013 | Watterson | G09B 19/00 434/247 |
| 2014/0074491 | A1 * | 3/2014 | Escorcia | A63B 24/0062 705/2 |
| 2014/0173082 | A1 * | 6/2014 | Shin | H04L 67/06 709/223 |
| 2014/0187383 | A1 * | 7/2014 | Martin | A63B 23/04 482/142 |
| 2014/0256512 | A1 * | 9/2014 | Kaiser | G16H 20/30 482/9 |
| 2014/0275821 | A1 * | 9/2014 | Beckman | A61B 5/6801 600/595 |
| 2014/0302967 | A1 * | 10/2014 | Ashby | A63B 24/0087 482/4 |
| 2015/0066171 | A1 * | 3/2015 | Brussog | H04L 67/04 700/91 |
| 2015/0119202 | A1 * | 4/2015 | Hendrickson | A63B 21/0051 482/54 |
| 2015/0134088 | A1 * | 5/2015 | Romeo | G16Z 99/00 700/91 |
| 2015/0141201 | A1 * | 5/2015 | Orgal | A61B 5/1114 482/8 |
| 2015/0157895 | A1 * | 6/2015 | Bettini | G16H 20/30 482/4 |
| 2015/0157896 | A1 * | 6/2015 | Soerensen | A63B 21/0552 482/8 |
| 2015/0258370 | A1 * | 9/2015 | Arkush | A61B 5/087 482/8 |
| 2015/0367175 | A1 * | 12/2015 | Alessandri | A63B 24/0075 482/8 |
| 2016/0189437 | A1 * | 6/2016 | Pyles | G06Q 40/08 482/8 |
| 2017/0056711 | A1 * | 3/2017 | Dalebout | A61B 5/6895 |
| 2017/0326411 | A1 * | 11/2017 | Watterson | A63B 22/0214 |
| 2018/0126248 | A1 * | 5/2018 | Dion | A63B 1/00 |
| 2018/0126249 | A1 * | 5/2018 | Consiglio | A63B 22/0023 |
| 2018/0272178 | A1 * | 9/2018 | Kennedy | A63B 22/02 |
| 2019/0224525 | A1 * | 7/2019 | Romero | A63B 21/0628 |
| 2020/0276073 | A1 * | 9/2020 | Hittel | A63B 69/0064 |
| 2020/0330818 | A1 * | 10/2020 | Thomas | A63B 21/062 |

* cited by examiner

EXERCISE APPARATUS WITH EXERCISE USE VERIFICATION FUNCTION AND VERIFYING METHOD

CROSS-REFERENCE TO RELATED APPLICATION

This application is a continuation-in-part of U.S. application Ser. No. 17/210,031, filed on Mar. 23, 2021, which is a continuation-in-part of U.S. application Ser. No. 17/026,847, filed on Sep. 21, 2020, which is a continuation of U.S. application Ser. No. 16/043,925, filed on Jul. 24, 2018, now U.S. Pat. No. 10,796,375, which is a continuation of U.S. application Ser. No. 14/983,171, filed on Dec. 29, 2015, now U.S. Pat. No. 10,032,227, which claims priority to U.S. Provisional Patent Application No. 62/098,309, filed on Dec. 30, 2014, of which the entire contents of all are incorporated herein by reference.

BACKGROUND

The present disclosure relates to an exercise apparatus. More particularly, the present disclosure relates to an exercise apparatus with exercise use verification function and verifying method.

Some insurance companies often give their customers a choice of paying more or proving that they regularly exercise. Clearly, if the customers demonstrate measurable healthy habits, including proof of regular exercise, the insurance companies can often pay less money toward insurance payouts, and can then pass a portion of these savings onto their customers. Under this arrangement, the insurance companies would encourage their customers to regularly exercise and keep healthy. In this situation, the customers stay healthy, there are fewer expensive insurance payouts due to poor health, and it is more profitable for the insurance companies. In order to demonstrate beneficial exercise habits of an insurance customer to their insurance company, a conventional exercise apparatus with an exercise use data reporting function (such as the embodiments disclosed in U.S. Pat. Nos. 8,287,434 and 6,638,198) comes to the world.

U.S. Pat. Nos. 8,287,434 and 6,638,198 both disclose a conventional exercise apparatus that can provide exercise use data therefrom for a user. The exercise use data would represent an exercise amount of the user. The user could demonstrate his (or her) exercise habit and exercise use to their insurance company, via this data. The conventional exercise apparatus comprises an operating member and a controller associated with the operating member. When the user drives the operating member to operate the exercise apparatus, the controller associated with the operating member creates exercise use data. Thereafter, the controller records the exercise use data and reports the exercise use data to the user. The user could use this exercise use data to demonstrate his (or her) exercise habit. Provided with this exercise use data, the user's insurance company may then offer discounts to the user.

Currently, exercise use data is restricted to exercise apparatus with a user-driven operating member, which is driven by the user to operate the exercise apparatus. Examples of a user-driven operating member of an exercise apparatus would be a stationary bike operating member (a crank shaft, driven by the bike pedals) or an elliptical trainer operating member (a crank shaft, driven by the elliptical pedals and linkage system). Currently, if the controller is set to record exercise use data on an exercise apparatus with motor-driven operating member, such as a treadmill operating member (a motor driven running belt) or a stairclimber operating member (a motor driven staircase), it would be easy to falsify exercise use data on the exercise apparatus. The user could just turn on a motor-driven operating member of an exercise apparatus, without actually using the exercise apparatus, and let a controller associated with the operating member create exercise use data. A specific example would be a user turning on a motorized treadmill, causing the running belt to move, and letting the treadmill run until the treadmill controller had recorded a large distance traveled by the running belt. The user would not need to be present on the treadmill, and yet the treadmill controller would record exercise use data. As a result, the controller thereof would record the exercise use data which is faked. To avoid this, manufactures have, to date, reported only exercise use data associated with user-driven operating members to insurance companies, because the faked exercise use data shouldn't represent the exercise habit or amount of user exercise to the insurance companies. In other words, exercise apparatus with motor-driven operating members currently on the market wouldn't help the user to demonstrate his (or her) exercise habits to an insurance company. Therefore, if one buys an exercise apparatus with a motor-driven operating member, he (or she) couldn't demonstrate his (or her) exercise habits via the exercise apparatus, because there is a question as to the validity of this exercise use data.

SUMMARY

The present invention has arisen to mitigate and/or obviate the disadvantages of the conventional exercise apparatus. Further benefits and advantages of the present invention will become apparent after a careful reading of the detailed description with appropriate reference to the accompanying drawings.

The present invention involves an exercise apparatus with exercise use verification function and a verifying method. Generally speaking, the exercise apparatus with exercise use verification function is to verify an exercise use thereof, and the verifying method is to verify an exercise use of an exercise apparatus. Therefore, for example, a user could demonstrate his (or her) exercise habit to their insurance company.

The invention provides, in one aspect, a motorized treadmill provided for allowing a user to perform a programed workout includes a base, an endless belt movable relative to the base for allowing a user to exercise thereon, a motor coupled to the endless belt for driving the endless belt to rotate, a signal receiver configured to receive a weight training signal, and a controller in communication with the signal receiver. When the user performs the programed workout with free weight equipment, the signal receiver will receive the weight training signal. The controller is configured to transmit validated exercise use data to a communication interface when the user is engaging the endless belt. When the signal receiver receives the weight training signal, the controller determines that the user is not engaging the endless belt and stops transmitting the validated exercise use data to the communication interface.

Preferably, the free weight equipment has a signal transmitter embedded therein. When the free weight equipment is operated by the user, the signal transmitter transmits the weight training signal to the signal receiver of the motorized treadmill. The controller is configured to generate the validated exercise use data when the endless belt is driven by the motor and to generate non-validated exercise use data when the signal receiver receives the weight training signal.

The invention provides, in another aspect, a system includes a motorized treadmill having an endless belt and a motor coupled to the endless belt for driving the endless belt to rotate for allowing a user to exercise thereon, at least one free weight equipment provided for allowing the user to perform free weight workout, at least one signal transmitter connected to the free weight equipment and configured to transmit a weight training signal when the free weight equipment is in operation, a signal receiver configured to receive the weight training signal from the free weight equipment, and a controller in communication with the motorized treadmill and the signal receiver. The controller is configured to transmit exercise use data while the motor drives the endless belt and stop transmitting the exercise use data when the signal receiver receives the weight training signal from the free weight equipment.

The invention provides, in yet another aspect, a method of verifying use of an exercise apparatus includes operating an operating member driven by a motor, generating exercise use data in response to operation of the operating member, transmitting the exercise use data by a controller to a communication interface while the operating member is driven by the motor, and stopping transmitting the exercise use data to the communication interface if the exercise apparatus receives a weight training signal from free weight equipment. The weight training signal is transmitted from the free weight equipment when the free weight equipment is in use.

The invention provides, in another aspect, a method of verifying the use of an exercise apparatus that includes operating a motor-driven operating member, generating a non-validated exercise use data in response to operating the motor-driven operating member, detecting engagement of the motor-driven operating member by a user, recording the non-validated exercise use data as validated exercise use data for a portion of time in response to detecting engagement of the motor-driven operating member by the user, and reporting the validated exercise use data to a communication interface.

The invention provides, in yet another aspect, a motorized treadmill that includes a base, an endless belt movable relative to the base, a motor operably coupled to the endless belt, a sensor configured to detect engagement of the endless belt by a user, and a controller configured to record validated exercise use data in response to the sensor detecting of engagement of the endless belt by the user, the validated exercise use data including an amount of user exercise time, the amount of user exercise time being generated by an amount of time that the sensor detects engagement of the endless belt by the user.

The reader is advised that this summary is not meant to be exhaustive. Further features, aspects, and advantages of the present invention will become better understood with reference to the following description, accompanying drawings and appended claims.

Further benefits and advantages of the present invention will become apparent after a careful reading of the detailed description with appropriate reference to the accompanying drawings.

DETAIL DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically depicted in order to simplify the drawings.

Figure 1:
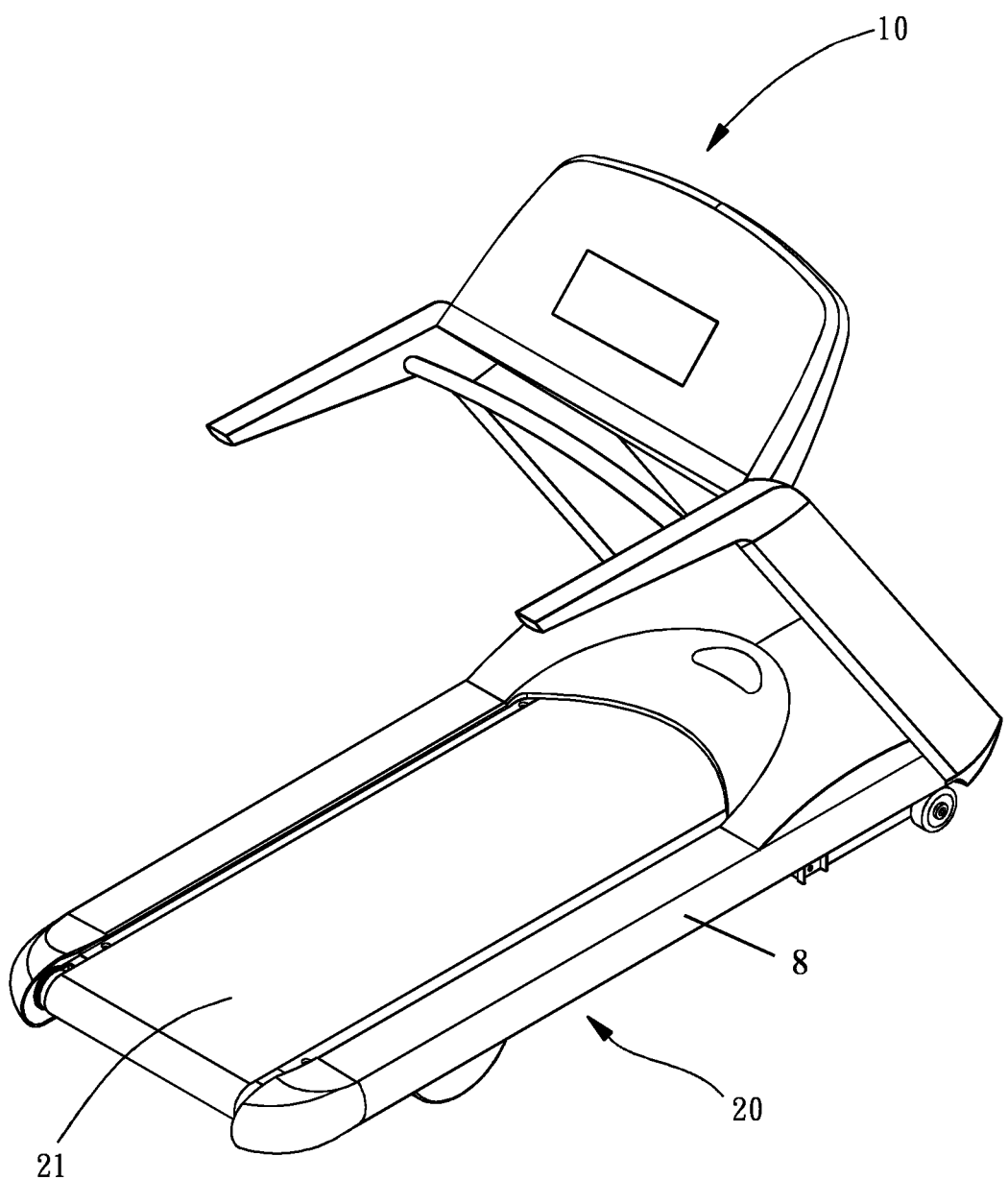
FIG. 1 is a perspective view of an exercise device embodying the present invention.
Figure 2:
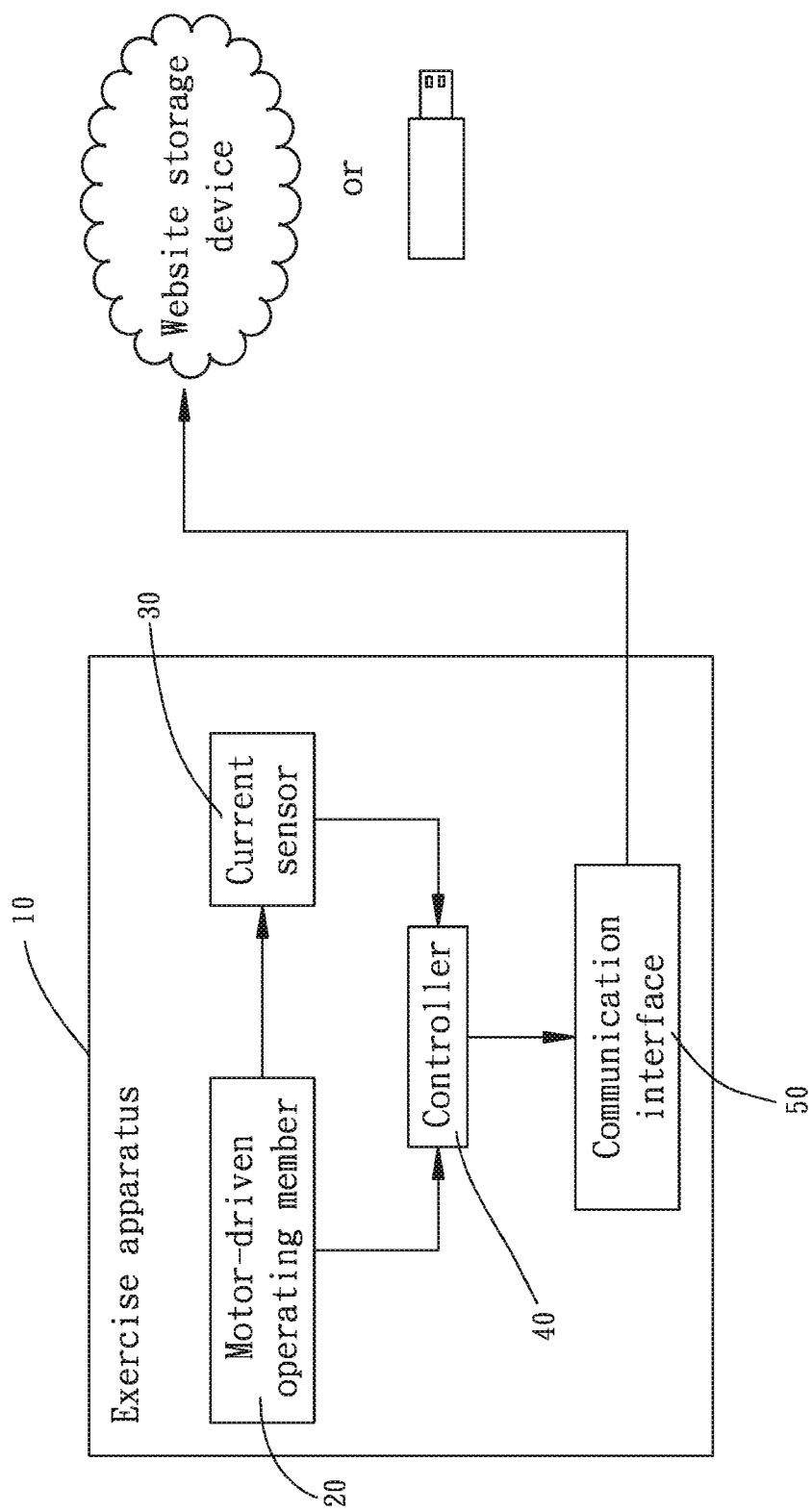
FIG. 2 is a schematic drawing of the exercise device and a data storage embodying the present invention.

FIGS. 1-2 illustrate an exercise apparatus 10 with an exercise use verification function. The exercise apparatus 10 comprises a base 8, a motor-driven operating member 20, a current sensor 30, a controller 40 associated with the motor-driven operating member 20 and the current sensor 30, and a communication interface 50 associated with the controller 40. Examples of an exercise apparatus can include a motorized treadmill (the embodiment of the present invention as shown in FIG. 1), a motorized stairclimber, or any other suitable types of motorized exercise equipment. In the embodiment illustrated in FIG. 1, the motor-driven operating member 20 includes an endless belt. It should be appreciated that the endless belt is provided for purposes of illustration, and the motor-driven operating member can be any suitable operating unit or operating member that a user of the exercise apparatus engages, contacts, or otherwise uses to perform the exercise. As an additional, non-limiting example of the motor-driven operating member, the exercise apparatus 10 can be a motorized stairclimber with the motor-driven operating member being a moving staircase.

Figure 3:
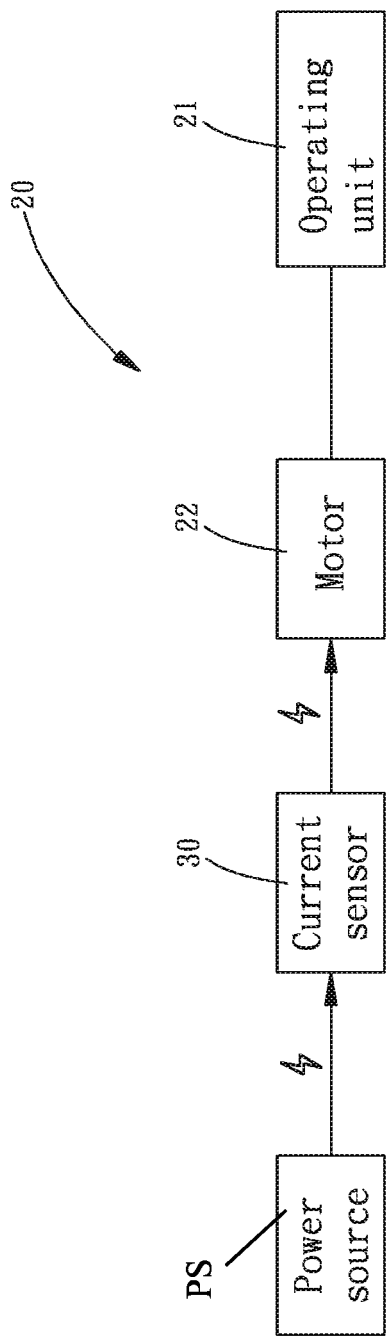
FIG. 3 is a schematic drawing of a motor-driven operating member and a power source embodying the present invention.

Referring to FIGS. 2-3, the motor-driven operating member 20 has an operating unit 21 (e.g., an endless belt, a staircase, etc.) and a motor 22. The motor 22 is structurally coupled to the operating unit 21 at one portion thereof. The motor 22 is electrically connected to a power source PS, such as an AC power socket, via a wire. The power source PS transmits an input current into the motor 22 via the wire so as to power the motor 22 to drive the operating unit 21. The current sensor 30 is associated with the motor 22 by being positioned between the motor 22 and the power source PS. The current sensor 30 is configured to detect the input current in the wire, and generate a current signal proportional to the input current (the detail of the current sensor, such as how to detect electrical current in a wire or generate a signal, is well-known and will not be further described here).

The controller 40 is operable to receive data according to operation of the motor-driven operating member 20, and further operable to process the data. In the illustrated embodiment, the controller 40 includes a microcontroller unit, at least one electronic circuit, and at least one circuit board. The microcontroller unit and the electronic circuit are assembled on the circuit board so as to define a controller assembly. In other embodiments, the controller 40 can be a computer processing system that includes a hardware assembly, a software assembly, and/or a firmware assembly. The hardware assembly of the controller 40 can include a processor that is in communication with a computer readable storage medium. The computer readable storage medium can be any suitable data storage device that can store data that can be thereafter accessed and read by the controller (or components thereof) or a separate computing system. Examples of computer readable storage medium can include, but is not limited to, read-only memory, CD-ROM, CD-R, CD-RW, DVD, DVD-RW, magnetic tapes, Universal Serial Bus (USB) flash drive, or any other optical or other suitable data storage device.

As illustrated in FIG. 2, the controller 40 is in communication with the motor-driven operating member 20 and the current sensor 30. In addition, the current sensor 30 is in communication with the motor-driven operating member 20. The controller 40 is in communication with the communication interface 50. The communication between components can be by any suitable wired connection (e.g., a bus wire, etc.), any suitable wireless connection (e.g., Bluetooth, Wi-Fi, etc.), or a combination of suitable wired and wireless connections. The communication interface 50 facilitates transmission or communication of exercise use data (validated and/or non-validated) from the exercise apparatus 10 for distribution. The communication interface 50 is discussed in additional detail below.

In operation, the current signal is transmitted from the current sensor 30 to the controller 40. Consequently, the controller 40 can continue to monitor a state of the input current. Specially, if a user gets on the operating unit 21 during operation of the motor-driven operating member 20 (e.g., the endless belt illustrated in FIG. 1), the motor 22 will draw more current because the operating unit 21 undertakes the user footfall and needs more driving power from the motor 22 to keep regularly operating. Therefore, the current sensor 30 will detect whether or not the user is engaging the motor-driven operating member 20 by detecting a current change of the input current that is caused by the user footfall. Thereafter, the current sensor 30 transmits the current signal proportional to the input current to the controller 40, so that the controller 40 can further determine, via the current signal, whether or not the user is engaging (or continues to engage, or ceases to engage) the motor-driven operating member 20.

Referring back to the first embodiment of FIGS. 1-3, if the operating unit 21 is driven by the motor 22, the controller 40 creates a non-validated exercise use data according to operation of the motor-driven operating member 20. Simultaneously, the current sensor 30 detects the input current in the wire to the motor 22 so as to detect whether or not a user is engaging the motor-driven operating member 20, and generates a current signal proportional to the input current. Then, the current signal is transmitted from the current sensor 30 to the controller 40. In order to determine whether or not a user is engaging the motor-driven operating member, the controller 40 analyzes fluctuations in the input current. Fluctuations occur when a user is using the exercise apparatus 10 due to the user's foot contacting the operating unit 21 and briefly causing a change in resistance to movement of the operating unit 21. This change in resistance is met by a change in input current to the motor 22. The controller 40 can be programmed to analyze the amplitude and frequency of any fluctuations in order to determine whether or not a user is using the exercise apparatus. Such an analysis can be tailored to distinguish user-induced fluctuations from fluctuations caused by other factors, such as belt or roller imbalance. The user-induced fluctuations sensed when a user is using the exercise apparatus 10 and not be sensed when a user is not using the exercise apparatus 10.

For example, the controller 40 can be programmed to detect that a user is engaging the operating member 20 if fluctuations of the input current are at least 5% and are at a frequency of between 80/minute and 250/minute. The parameters will vary depending on the exercise apparatus, and can be chosen to distinguish from normal fluctuations in the motor, transmission, and belt.

Figure 4:
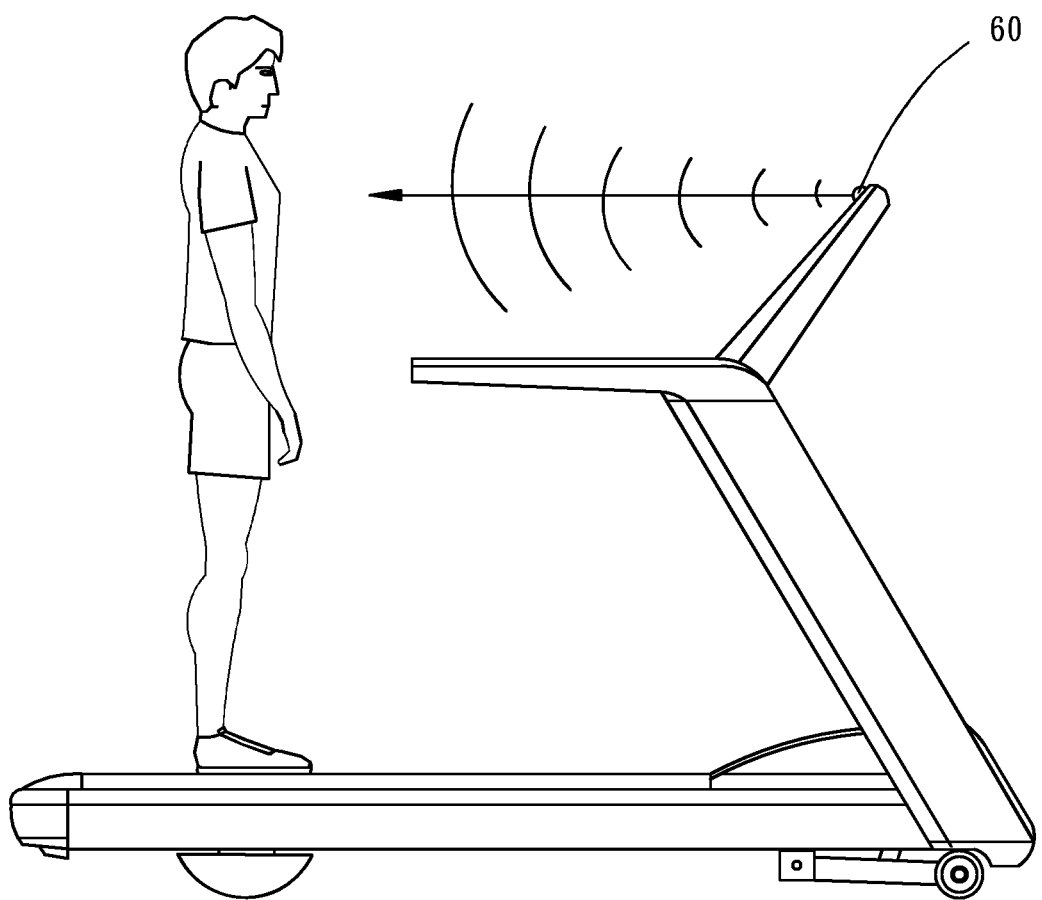
FIG. 4 is a side view of a second embodiment of the present invention.
Figure 5:
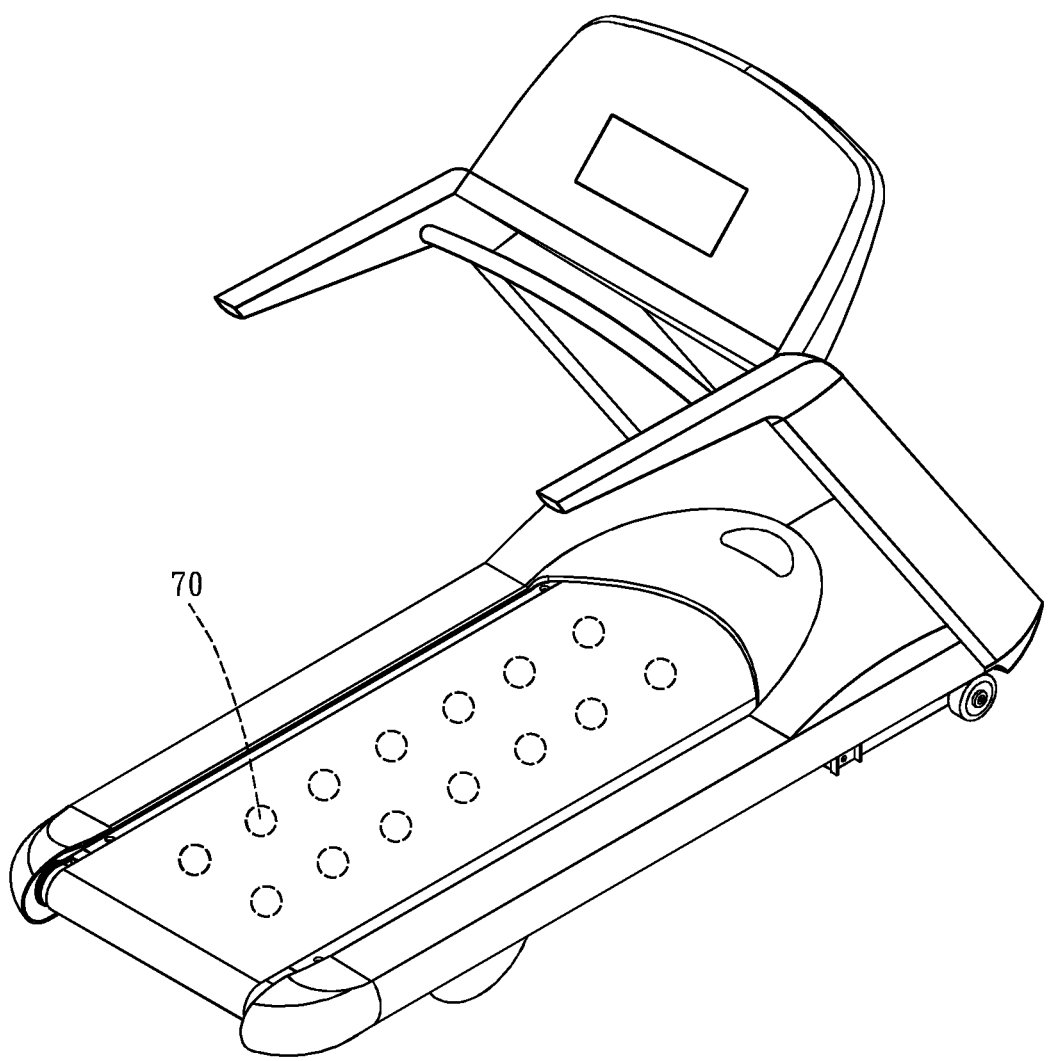
FIG. 5 is a perspective view of a third embodiment of the present invention.

Although a sensor that is configured to detect whether or not a user is engagement with the motor-driven operating member is illustrated in the embodiment of FIGS. 1-3 as the current sensor 30, in other embodiments other sensors can be implemented. For example, in other embodiments the sensor for detecting user engagement of the motor-driven operating member can be an optical sensor 60 that senses a level of IR radiation (see FIG. 4), a pressure sensor 70 that senses (or detect) an amount of pressure on the running belt (see FIG. 5), a speed sensor that senses fluctuations in speed of the operating unit, a thermal sensor that senses a level of heat (i.e., from a human body) on or near the motor-driven operating member, or any other suitable sensor. In each of these cases, the measured parameter can be compared to a default parameter that exists when a user is not engaging the motor-driven operating member. The detail of these sensing devices is well-known and will not be further described here.

If the user is not detected as engaging the motor-driven operating member 20, the controller 40 keeps creating non-validated exercise use data and monitoring the state of the input current in the wire to the motor 22. In contrast, if the user is detected as engaging the motor-driven operating member 20, the controller 40 records the non-validated exercise use data as validated exercise use data. Finally, the validated exercise use data is reported from the controller 40 to the communication interface 50. The validated exercise use data can further include an amount of time (or portion of time or accrued amount of time) the user is detected as engaging the motor-driven operating member 20 (i.e., the amount of time the user spends exercising), which can be based on a timer or other timing device that measures the amount of time the user is detected as engaging the motor-driven operating member 20. In addition, or alternatively, the validated exercise use data can include a distance traveled (or an equivalent distance traveled) by the user while the user is detected as engaging the motor-driven operating member 20 (i.e., the distance traveled by the user while exercising).

The communication interface 50 can communicate the exercise use data (e.g., validated and/or non-validated exercise use data) to an interested third party (e.g., a physician, a medical provider, etc.), a demander (e.g., an insurance company, an insurance provider, etc.), and/or the user. For example, the communication interface 50 can be a display device, such as a screen of a console positioned on a portion of the exercise apparatus 10. The screen can be configured to display the validated exercise use data to the user. The user is then free to view and/or document (e.g., write down, etc.) the validated exercise use data so as to present it to the interested third party and/or demander. In this way, the validated exercise use data is substantially shown as a multimedia content, such as a media image and/or a sound. As another example, the communication interface 50 is configured to output the exercise use data to an outside storage device such as a flash drive, a disk rewriter, or a website storage device by a communication link. The communication link can be a port (or plug) that is configured to receive a computer readable storage medium (e.g., a USB flash drive, etc.). The validated exercise use data is substantially packaged in a computer file that can be accessed or processed to show the validated exercise use data as a multimedia content, such as the media image and/or the sound. Additionally or otherwise, the communication link can be a wired connection (e.g., a USB connection, a CAT-5 connection, etc.) or a wireless connection (e.g., an Internet interface, Wi-Fi, Bluetooth, etc.). In this way, the port (or plug) is replaced with (or can also further include) a wired and/or wireless communication module, and the outside storage device has a further corresponding wired and/or wireless communication module. The validated exercise use data can then be transmitted from the communication module of the exercise apparatus 10 to the communication module of the outside storage device (by the wired and/or wireless connection). In the illustrated embodiment shown in FIGS. 1-3, the communication interface 50 is illustrated as an Internet interface, such as a Wi-Fi internet module or an internet port. It should be appreciated that the outside storage device can be a web or Internet based storage device, such as a web based database. This allows for the communication of validated exercise use data to the interested third party or demander by via wireless internet connection or wired internet connection. Therefore, the user does not need to manually present the validated exercise use data to the interested third party or demander. In other examples of embodiments, the communication interface 50 can be programmed or incorporated into the controller 40 such that the controller 40 performs the functions associated with the communication interface 50 as described herein.

Figure 6:
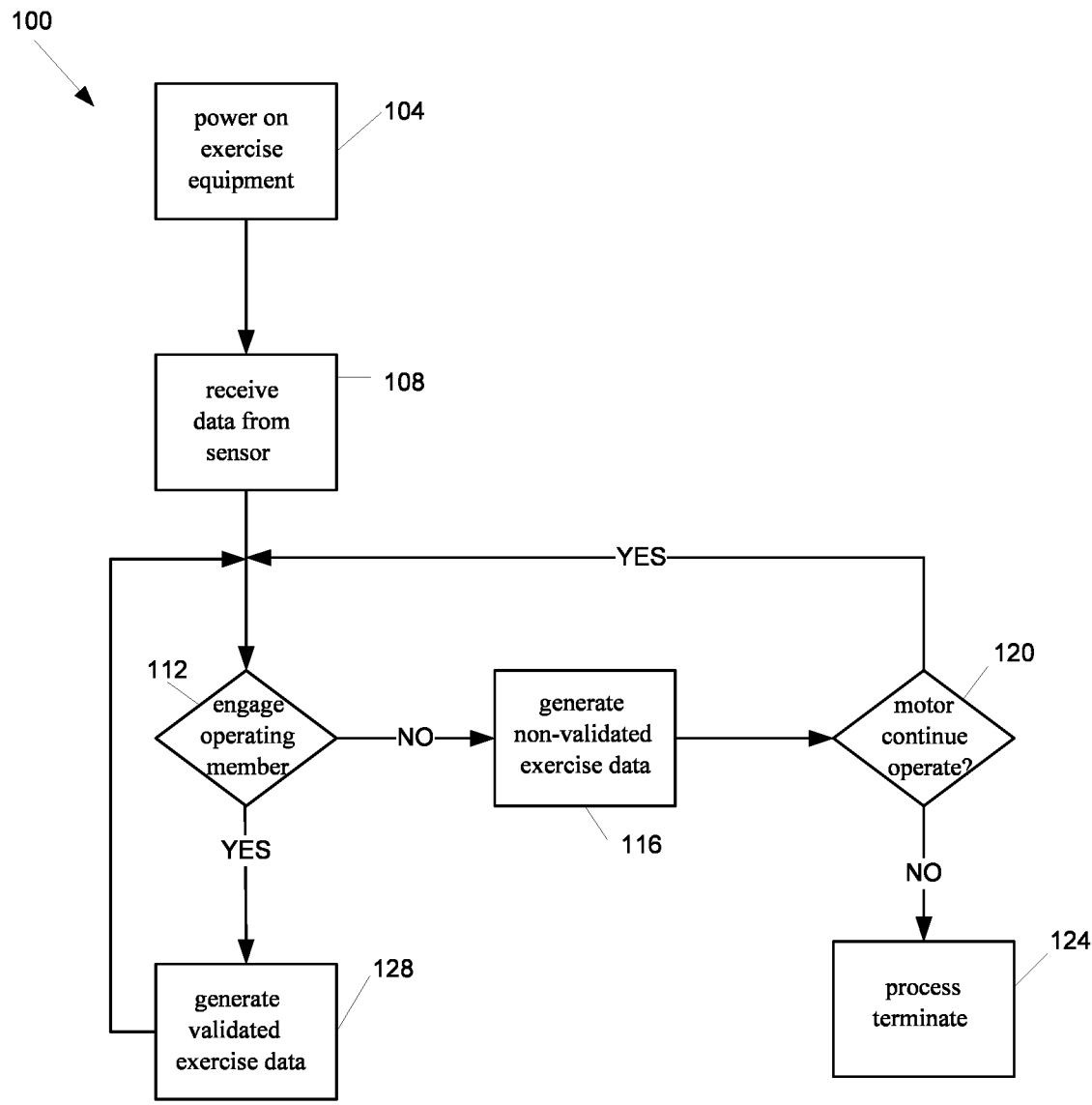
FIG. 6 is a flow diagram of an embodiment of an exercise use verification application that verifies use of the exercise device.

FIG. 6 illustrates an example of an exercise use verification application 100 that uses data acquired from the motor-driven operating member 20 to monitor and verify that a user is using the exercise equipment. The application 100 can be a module that operates on (or is associated with) the controller 40. The application 100 may be distributed and stored on the controller 40, and/or can be accessible from a remote location, such as through a web portal, web site, local area network, or generally over the Internet. The exercise use verification application 100 includes a series of processing instructions or steps that are depicted in flow diagram form.

Referring to FIG. 6, the process begins at step 104, where the exercise apparatus 10 is powered on and in an operational state. The application 100 is initiated, for example, by an interlock with the motor 22 such that when the motor 22 is in an operational state, the application 100 is also operational.

Next, at step 108 the controller 40 receives data from the sensor configured to detect user engagement with the exercise apparatus 10. For example, the controller 40 receives data from the current sensor 30. In other embodiments, the controller 40 receives data from the optical sensor 60, the pressure sensor 70, the speed sensor, the thermal sensor, or the other suitable sensor.

Proceeding to step 112, the controller 40 analyzes the data from the sensor to detect whether a user is actively engaging the motor-driven operating member 20. For example, the controller 40 can analyze fluctuations in the input current from the current sensor 30, as described above. In addition, or alternatively, the controller 40 can compare the received data from the sensor to a known (or default or standard) data parameter that is indicative of a user not engaging the motor-driven operating member 20. The known data parameter can be preprogrammed into the controller, or recognized during operational use (e.g., operation of the motor-driven operating member 20 without a user). If the analysis results in a "no," there is no user detected that is actively engaging the motor-driven operating member 20, the process proceeds to step 116. If the analysis results in a "yes," there is a user detected that is actively engaging the motor-driven operating member 20, the process proceeds to step 128, the details of which are later described.

At step 116, the process generates non-validated exercise use data. This data can be locally stored, or communicated to an interested third party, a demander, and/or the user as discussed above. Next, at step 120, the process detects whether the motor 22 (or motor-driven operating member 20) continues to operate. If the process detects that "yes" the motor 22 continues to operate, the process returns to step 112 and repeats. If the process detects that "no" the motor 22 does not continue to operate, which is indicative of the exercise apparatus 10 no longer operating, the process terminates at step 124.

At step 128, the process generates validated exercise use data. More specifically, the controller can record (or otherwise identify) the non-validated exercise use data as validated exercise use data. The validated exercise use data can be locally stored or communicated to an interested third party, a demander, and/or the user as discussed above. The process returns to step 112 and repeats.

Figure 7:
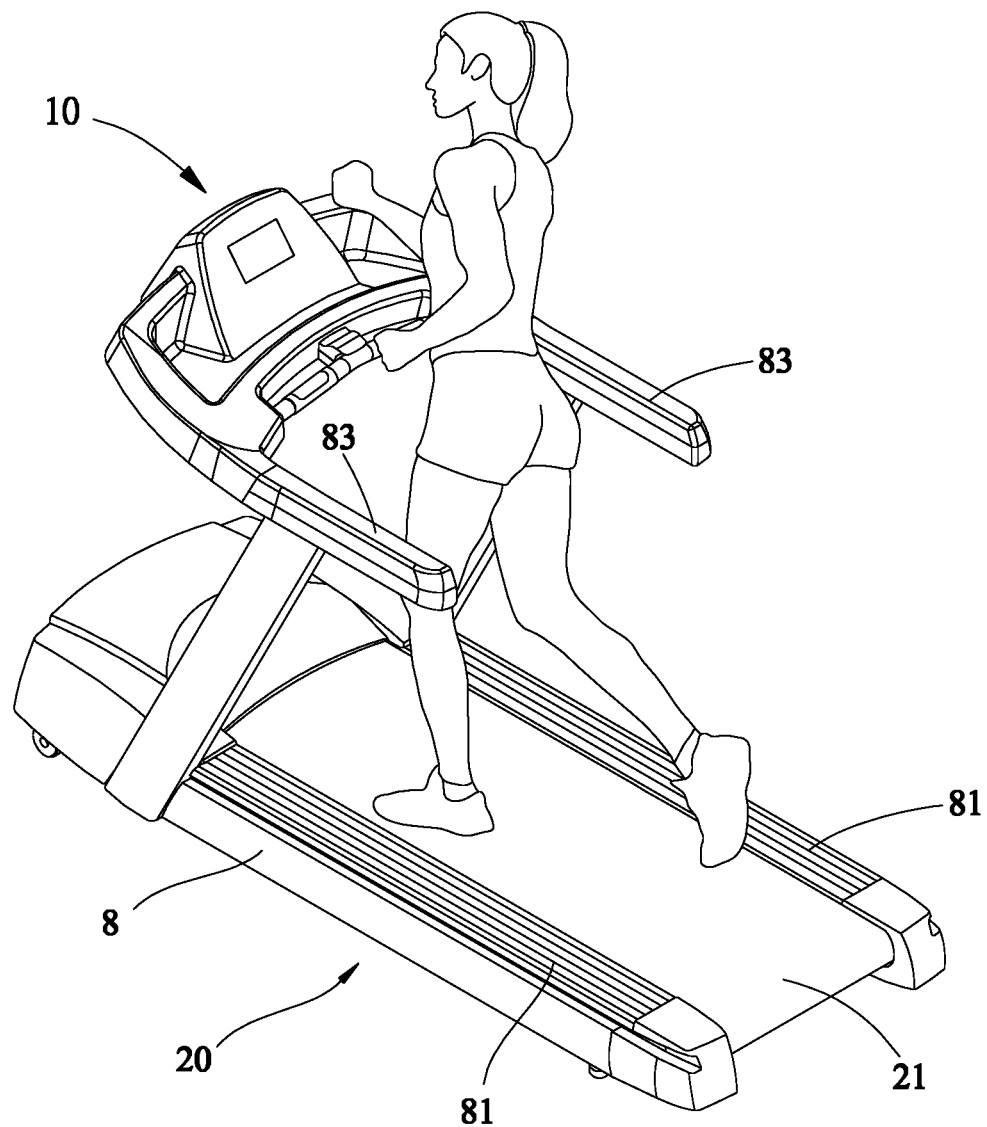
FIG. 7 illustrates a user using a motorized treadmill normally.

FIG. 7 illustrates an example of a user performing an exercise on an exercise apparatus normally. More specifically, the user is running or walking on a motorized treadmill 10 with both feet. As described above and referring to FIG. 2, the motorized treadmill 10 has a motor-driven operating member 20, a current sensor 30, a controller 40, and a communication interface 50. The motor-driven operating member 20 has an endless belt 21 and a motor 22 coupled to the endless belt 21 for driving the endless belt 21 to rotate, so that the user is able to do exercise of walking, jogging, or running on the endless belt 21. The current sensor 30 is configured to detect the input current into the motor 22 during rotation of the endless belt 21, and generate a current signal proportional to the input current. The controller 40 is in communication with the motor-driven operating member 20 and the current sensor 30. The communication interface 50 is in communication with the controller 40.

In general, when using the motorized treadmill 10, the user is supposed to have both feet "fully contacting" the endless belt 21 (i.e., with the person's full weight) to perform walking, jogging, or running on the endless belt 21 while the motor drives the endless belt 21 to rotate, as shown in FIG. 7. If the endless belt 21 is driven by the motor 22, the current sensor 30 will transmit the current signal to the controller 40, and the controller 40 is operable to determine whether or not the user is engaging the endless belt 21 via the current signal. The controller 40 is configured to transmit validated exercise use data to the communication interface 50 when the controller 40 determines that the user is engaging the endless belt 21 to do exercise.

Figure 8:
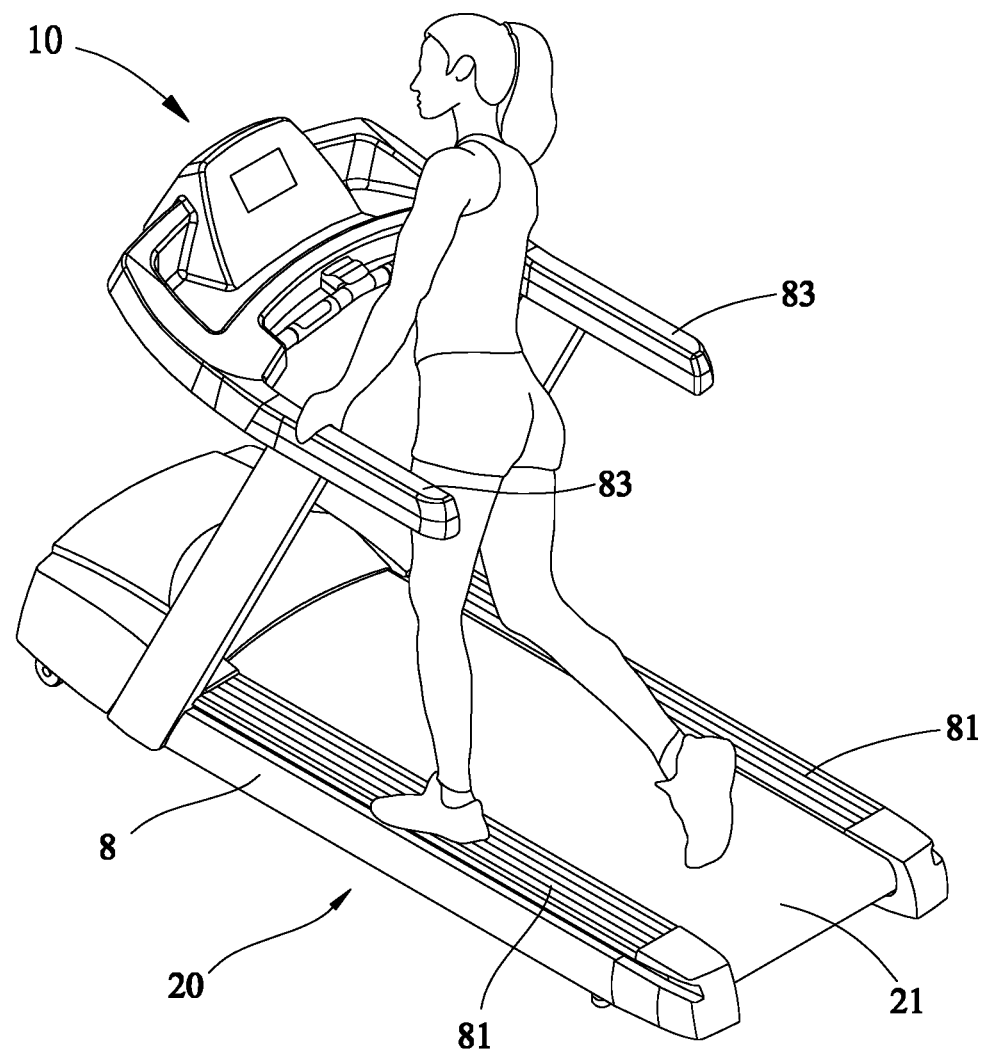
FIG. 8 illustrates the user using the motorized treadmill with only one foot.

Referring to FIG. 7, the motorized treadmill 10 has a base 8, two foot rails 81 disposed on the two sides of the endless belt 21, and two hand rails 83. The user can stand on either of the two foot rails 81 before, during, or after using the motorized treadmill 10. In a specific situation, if the user stands on one foot rail 81 by one foot and steps periodically on the endless belt 21 by the other one foot as shown in FIG. 8, the controller 40 may determine that the user is still engaging with the endless belt 21 and continue transmitting validated exercise use data to the communication interface 50. Similarly, in another specific situation, if the user grasps and supports a portion of the user's weight on the hand rails 83, the user could lightly contact the endless belt 21 with the user's feet, and the controller 40 may determine that the user is still engaging with the endless belt 21 and continue transmitting validated exercise use data to the communication interface 50 even though the user's feet are not fully contacting the belt. As a result of either situation, the controller 40 thereof would record the exercise use data, which is faked. In order to avoid this, in addition to detecting current pulses associated with the periodic contact of a user's foot with the belt, it is desirable for the controller 40 to further determine whether or not both feet of the user are fully contacting the endless belt (i.e., with the user's full weight) while exercising.

Figure 9A:
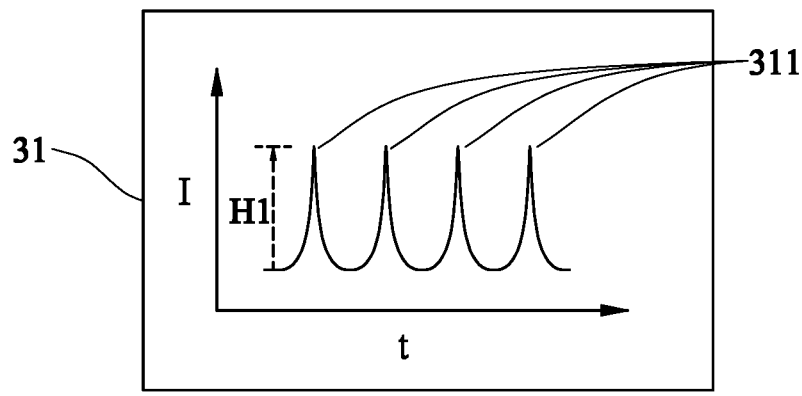
FIGS. 9a-9c illustrate plots of current verses time for showing changes of input current to a motor during operation of the motor of the motorized treadmill.
Figure 9B:
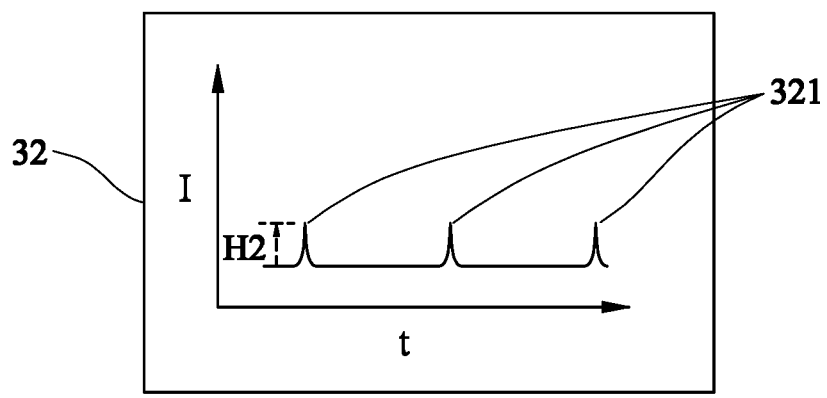
Figure 9C:
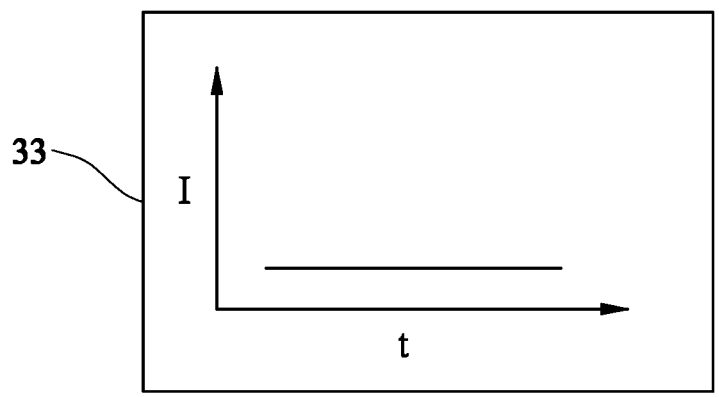

In a preferred embodiment, the controller 40 can be programed to analyze the amplitude or frequency of fluctuations in the input current to determine whether or not both feet of the user are fully contacting the endless belt 21 while the motor 22 drives the endless belt 21. As mentioned before, fluctuations in the input current occur when the user is using the motorized treadmill 10 due to the user's foot contacting the endless belt 2 and causing a change in the input current to the motor 22. FIGS. 9a-9c illustrate plots of current verses time for showing changes of the input current during operation of the motor 22 under three different conditions. When the user is walking, jogging or running on the endless belt 21 of the motorized treadmill 10 under normal conditions, each foot fully contacts the endless belt 21 and causes an increase in the input current into the motor 22 for keeping the endless belt 21 moving at the same rate. As shown in FIG. 9a, the increase of the input current may be represented as a current pulse 311 in a plot 31, namely each current pulse 311 represents one footfall of the user on the endless belt 21. The current pulses of the input current can be detected by the current sensor 30 and form a current signal, such that the controller 40 is able to analyze the amplitude and frequency of the input current via the current signal.

As shown in FIG. 9a, the plot 31 illustrates current changes with respect to time when a user is walking, jogging or running on the endless belt 21 normally, with both feet fully contacting the belt. The interval between adjacent two current pulses 311 represents a time interval between two steps while exercising on the endless belt 21. The plot 31 shows the input current to the motor 22 having a first frequency and a first amplitude H1. In contrast, FIG. 9b shows a plot 32 having current pulses 321 representing current changes with respect to time when the same user is using the motorized treadmill 10 abnormally, without both feet fully contacting the belt. For example, as shown in FIG. 8, the user has only one foot step periodically on the endless belt 21, causing the input current to the motor 22 having a second frequency and a second amplitude H2. For example, the first frequency may be in a range between 80 pulses/minute and 250 pulses/minute, namely in a stride frequency range between 80 steps/minute and 250 steps/minute, such that the controller 40 can determine that both feet of the user are fully contacting the endless belt 21 for normal walking, jogging or running. In contrast, the second frequency may be a frequency below 80 pulses/minute, namely below a stride frequency of 80 steps/minute, such that the controller 40 can determine that at least one foot of the user is not fully contacting the endless belt 21 even though a current pulse is detected by the current sensor 30 and the endless belt 21 is continuously driven by the motor 22, as shown in FIG. 8. Accordingly, the controller 40 can be programed to analyze the frequency of the input current to the motor 22 to determine whether or not the detected current frequency is above or below a threshold frequency, which is an indication whether or not both feet of the user are fully contacting the endless belt while exercising. It should be appreciated that the precise threshold frequency between validated and non-validated data could be altered depending on the situation, such as the exercise being performed (e.g., walking, jogging, running) and the typical stride frequency of the individual performing the exercise.

The controller 40 can also be programed to analyze the amplitude of the input current to the motor 22 to determine whether or not both feet of the user are treading on the endless belt with full force while exercising. For example, as shown in FIG. 9a and FIG. 9b, the second amplitude H2 is relatively lower than the first amplitude H1 (e.g. lower than 20% of the first amplitude H1), such that the controller 40 can determine that at least one foot of the user does not tread on the endless belt 21 or that the user is supporting at least a portion of the user's weight in the hand rails 83. As shown in FIG. 9c, when foot impacts are absent from the endless belt 21, the input current to the motor 22 does not have any pulse as illustrated in a plot 33. It should be noted that the motor 22 of the present invention can be a DC motor or an AC motor, which is not limited in the present invention.

Figure 10:
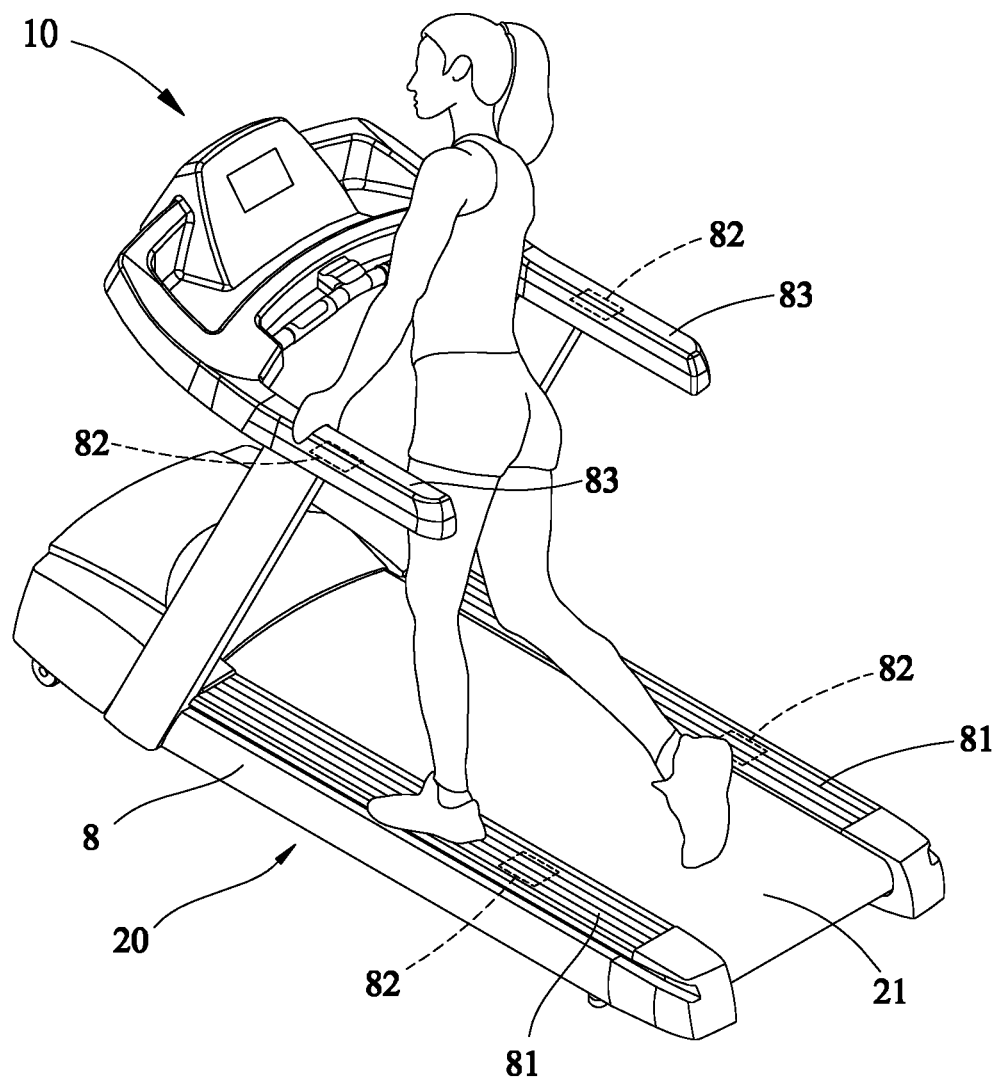
FIG. 10 is a perspective view of another embodiment of the present invention, wherein a motorized treadmill has a plurality of force sensors disposed under two foot rails of the motorized treadmill.

Under this arrangement, when the user uses the motorized treadmill 10, the controller 40 is able to determine that both feet of the user are contacting the endless belt 21 with the user's full weight or at least one foot of the user is not contacting the endless belt 21 while the motor 22 continues to drive the endless belt 21 to rotate according to changes of amplitude or frequency of fluctuations in the input current. When the frequency or amplitude of the input current is below a threshold frequency or threshold amplitude, the controller 40 can determine that at least one foot of the user is not fully contacting the endless belt 21 and stops transmitting validated exercise use data to the communication interface 50. In another embodiment, as shown in FIG. 10, the motorized treadmill 10 has a plurality of force sensors 82 disposed under the two foot rails 81 and/or hand rails 83 for detecting whether or not the user is standing on either of the two foot rails or grasping either of the two hand rails 83, respectively. When the force sensors 82 detect that any one foot of the user is standing on either of the two foot rails 81 or the user is grasping either of the hand rails for supporting a portion of the user's weight, the controller 40 is operable to stop transmitting validated exercise use data to the communication interface 50.

Figure 11:
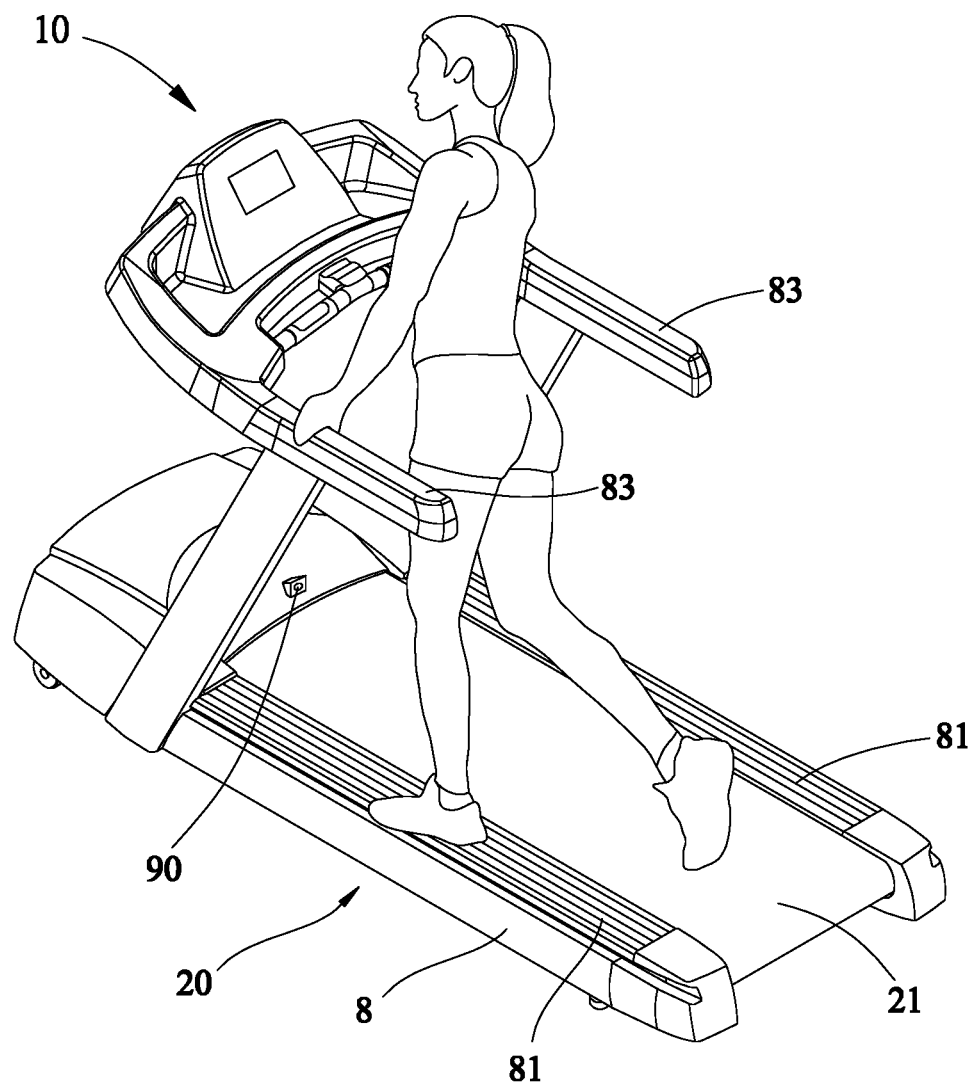
FIG. 11 is a perspective view of another embodiment of the present invention, wherein a motorized treadmill has an optical sensor for detecting the user.

In another embodiment, as shown in FIG. 11, the motorized treadmill 10 has an optical sensor 90 (e.g., a proximity sensor, and infrared sensor, or a camera) configured to detect whether or not the user is standing on either of the two foot rails 81. When the optical sensor 90 detects that any one foot of the user is standing on either of the two foot rails 81, the controller 40 is operable to stop transmitting validated exercise use data to the communication interface 50. A similar optical sensor could be positioned to detect whether or not the user is grasping either of the hand rails 83.

Figure 12:
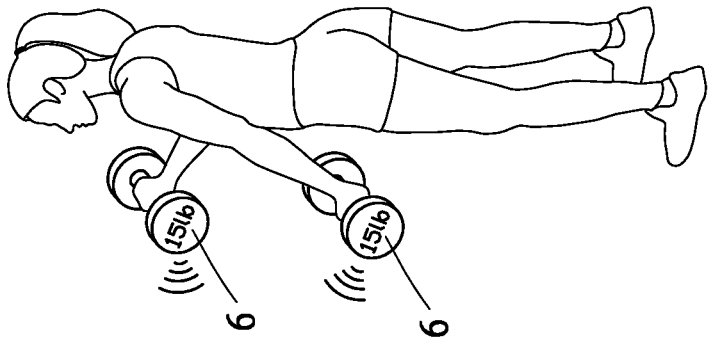
FIG. 12 is a perspective view of another embodiment of the present invention, wherein a motorized treadmill has an exercise use verification function by sensing presence of a user via weight training signal.
Figure 12:
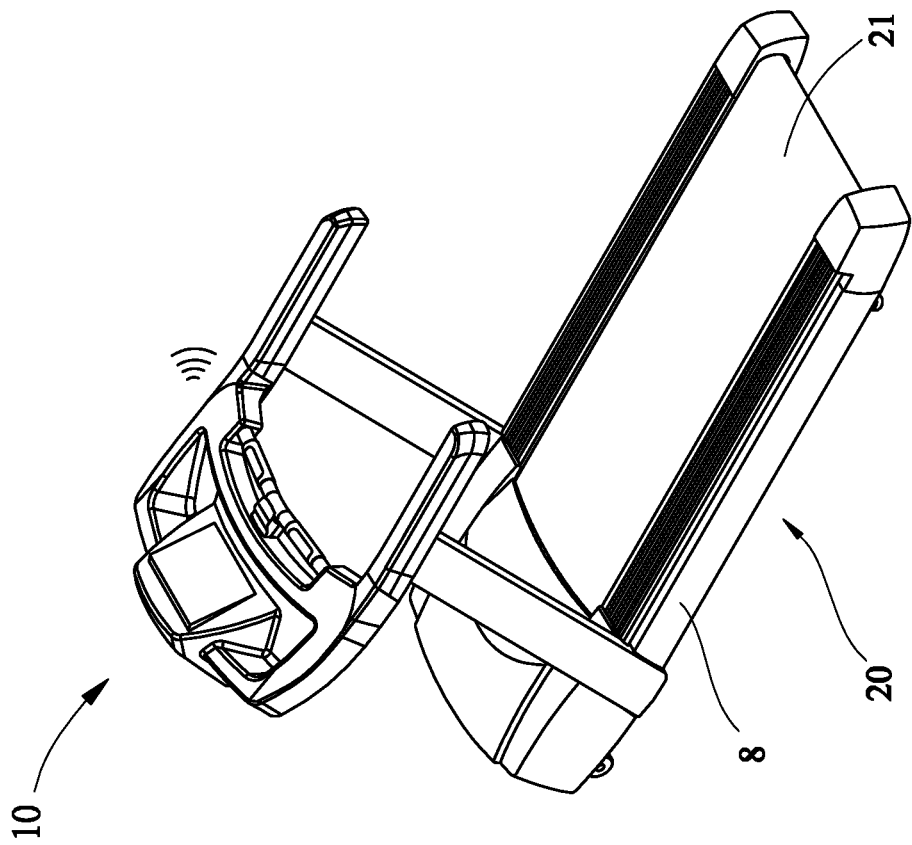
Figure 13:
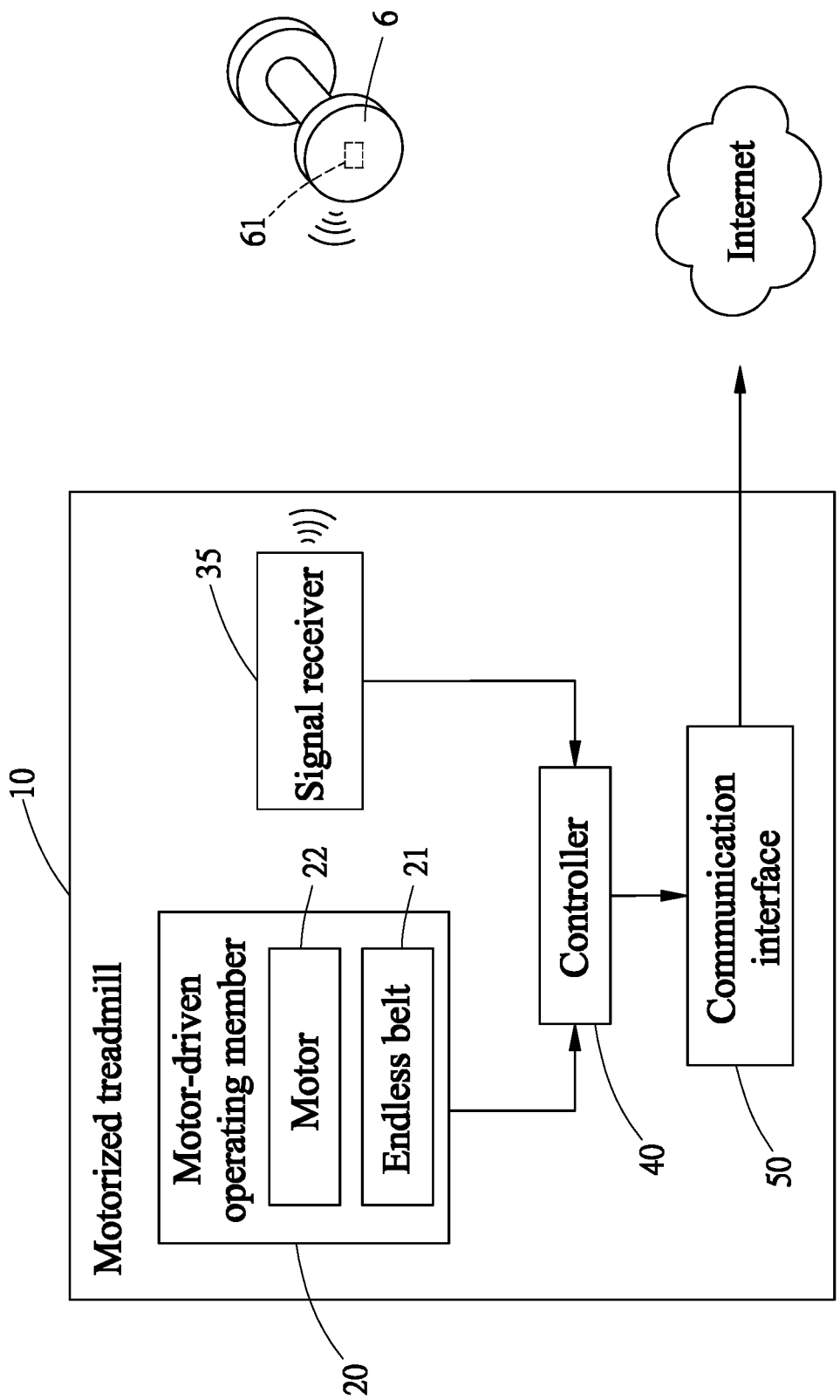
FIG. 13 is a schematic drawing of the motorized treadmill with exercise use verification function shown in FIG. 12.

FIGS. 12-13 illustrate another embodiment of an exercise apparatus such as a motorized treadmill 10 with an exercise use verification function. Similar to previous embodiments, the motorized treadmill 10 has a base 8, an endless belt 21 mounted around the base 8, and a motor 22 coupled to the endless belt 21 for driving the endless belt 21 to rotate. The endless belt 21 and the motor 22 constitute the aforementioned motor-driven operating member 20. The motorized treadmill 10 further includes a controller 40 associated with the motor-driven operating member 20 and a communication interface 50 in communication with the controller 40. The motorized treadmill 10 is provided for allowing a user to perform aerobic exercise such as walking, jogging, or running. When the motorized treadmill 10 is operated by the user, the endless belt 21 is driven by the motor 22 to rotate relative to the base 8 for allowing the user to exercise thereon. The controller 40 is operable to receive data according to operation of the endless belt 21 of the motorized treadmill 10. In general, the controller 40 includes a processor configured to process the received data and generate exercise use data. The controller 40 is able to record the exercise use data and report the exercise use data to the user.

The motorized treadmill 10 may be provided for allowing the user to perform a programed workout or an exercise course. The programed workout includes aerobic exercises and anaerobic exercises. For example, the user can use the motorized treadmill 10 to perform an aerobic exercise such as walking, jogging, or running; or the user can use free weight equipment 6 to perform an anaerobic exercise such as free weight training. The free weight equipment may include dumbbells, barbells, kettlebells, adjustable dumbbells, medicine balls, sandbells, weight plates, weighted bags, other types of free weights, or combinations thereof. When using the motorized treadmill 10, the user can tread on the endless belt 21 to perform the aerobic exercise of walking, jogging, or running while the motor 22 drives the endless belt 21 to rotate, as shown in FIG. 7. In this situation, the controller 40 determines that the user is engaging the endless belt 21 to perform aerobic exercise and transmits exercise use data to the user. In contrast, as shown in FIG. 12, when the user turns to perform anaerobic exercise, the user generally has to move away from the endless belt 21 to perform the anaerobic exercise such as free weight training. If the user moves away from the motorized treadmill 10 to perform the free weight training without stopping rotation of the endless belt 21, the endless belt 21 will be continuously driven by the motor 22, and the controller 40 will continue recording and transmitting the exercise use data which is faked. In order to avoid this, it is desirable for the controller 40 to further determine whether the motorized treadmill 10 is actually operated by the user.

FIGS. 12-13 depict an example of a system for verifying use of the motorized treadmill. For example, the user can choose to perform a programed workout or an exercise course including treadmill workout and dumbbell workout. In a preferred embodiment, there may be a dumbbell set 6 positioned beside the motorized treadmill 10 for allowing the user to perform the dumbbell workout during the programed workout or the exercise course. When the user lifts the dumbbell set 6 to perform the dumbbell workout (namely the free weight training), the motorized treadmill 10 will receive a weight training signal from the dumbbell set 6. Once the motorized treadmill 10 receives the weight training signal, the controller 40 will determine that the user is not engaging the endless belt 21 and stops transmitting the exercise use data associated with the motorized treadmill 10. In other words, when the user performs the dumbbell workout of the programed workout, the motorized treadmill 10 will be in an idle state and the controller 40 is programmed to stop transmitting the exercise use data associated with the treadmill workout, such that the data received from the motorized treadmill 10 will represent validated (or actual) exercise use data for the treadmill workout.

In the preferred embodiment, the free weight equipment 6 has at least one signal transmitter 61 embedded therein. The signal transmitter 61 is configured to transmit a weight training signal when the free weight equipment 6 is in operation. In general, the motorized treadmill 10 has a signal receiver 35 configured to receive the weight training signal from the signal transmitter 61 of the free weight equipment 6. For example, each dumbbell 6 may have a transmitter 61 embedded therein for sensing movement of the respective dumbbell 6. When the dumbbell 6 is operated by the user, the signal transmitter 61 will transmit a weight training signal to the signal receiver 35 of the motorized treadmill 10, which is indicative of the motorized treadmill 10 no longer operating, as shown in FIG. 12. The signal transmitter 61 includes, but not limited to, one or more accelerometers embedded in the free weight equipment 6. The accelerometer is configured to sense movement of the free weight equipment 6 (e.g., lifts of dumbbells). When the user uses the free weight equipment 6 to perform the free weight workout, the accelerometer will detect movement of the free weight equipment 6 and the signal transmitter 61 will transmit a weight training signal to the signal receiver 35 of the motorized treadmill 10 at the same time, so that the controller 40 can determine that the user is not engaging the endless belt 21 and stop transmitting exercise use data to the communication interface 50. In addition, if the controller 40 determines that the user is not engaging the endless belt 21 via the weight training signal but the motor 22 still drives the endless 21 to rotate, the controller 40 can be operable to stop operation of the motor 22 to stop rotation of the endless belt 21.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A motorized treadmill provided for allowing a user to perform a programed workout, comprising:
   a base;
   an endless belt movable relative to the base for allowing a user to exercise thereon;
   a motor coupled to the endless belt for driving the endless belt to rotate;
   a signal receiver configured to receive a weight training signal when the user performs the programed workout with free weight equipment; and
   a controller in communication with the signal receiver, the controller configured to transmit validated exercise use data when the user is engaging the endless belt, wherein when the signal receiver receives the weight training signal, the controller determines that the user is not engaging the endless belt and stops transmitting the validated exercise use data.

2. The motorized treadmill as claimed in claim 1, further comprising a communication interface in communication with the controller, wherein the controller is configured to transmit the validated exercise use data to the communication interface when the user is engaging the endless belt.

3. The motorized treadmill as claimed in claim 1, wherein the free weight equipment has a signal transmitter embedded therein, when the free weight equipment is operated by the user, the signal transmitter transmits the weight training signal to the signal receiver of the motorized treadmill.

4. The motorized treadmill as claimed in claim 3, wherein the signal transmitter includes one or more accelerometers embedded in the free weight equipment, the accelerometers configured to sense movement of the free weight equipment, and wherein when the user uses the free weight equipment to perform free weight workout, the signal receiver will receive a weight training signal from the free weight equipment, so that the controller determines that the user is not engaging the endless belt and stops transmitting the validated exercise use data.

5. The motorized treadmill as claimed in claim 1, wherein the programed workout includes an aerobic exercise and an anaerobic exercise, the user operating the motorized treadmill to perform the aerobic exercise and operating the free weight equipment to perform the anaerobic exercise.

6. The motorized treadmill as claimed in claim 1, wherein the controller is configured to generate the validated exercise use data when the endless belt is driven by the motor and to generate non-validated exercise use data when the signal receiver receives the weight training signal.

7. The motorized treadmill as claimed in claim 1, wherein the free weight equipment comprises dumbbells, barbells, kettlebells, adjustable dumbbells, medicine balls, sandbells, weight plates, weighted bags, other types of free weights, or combinations thereof.

8. The motorized treadmill as claimed in claim 1, wherein when the signal receiver receives the weight training signal, the controller is operable to stop operation of the motor to stop rotation of the endless belt.

9. A system, comprising:
a motorized treadmill having an endless belt and a motor coupled to the endless belt for driving the endless belt to rotate for allowing a user to exercise thereon;
at least one free weight equipment provided for allowing the user to perform free weight workout;
at least one signal transmitter connected to the free weight equipment and configured to transmit a weight training signal when the free weight equipment is in operation;
a signal receiver configured to receive the weight training signal from the free weight equipment; and
a controller in communication with the motorized treadmill and the signal receiver, the controller configured to transmit exercise use data while the motor drives the endless belt and stop transmitting the exercise use data when the signal receiver receives the weight training signal from the free weight equipment.

10. The system as claimed in claim 9, further comprising a communication interface in communication with the controller, wherein the controller is configured to transmit the exercise use data to the communication interface when the endless belt is driven by the motor without receiving the weight training signal.

11. The system as claimed in claim 9, wherein the signal transmitter includes one or more accelerometers embedded in the free weight equipment, the accelerometers configured to sense movement of the free weight equipment, and wherein when the user uses the free weight equipment to perform free weight workout, the signal receiver will receive a weight training signal from the free weight equipment, so that the controller determines that the user is not engaging the endless belt and stops transmitting the validated exercise use data.

12. The system as claimed in claim 9, wherein the motorized treadmill is provided for allowing the user to perform an aerobic exercise and the free weight equipment is provided for allowing the user to perform an anaerobic exercise, when the signal receiver receives the weight training signal, the controller determines that the user is performing the anaerobic exercise and stops transmitting the exercise use data of the aerobic exercise.

13. The system as claimed in claim 9, wherein the controller is configured to generate validated exercise use data when the endless belt is driven by the motor and to generate non-validated exercise use data when the signal receiver receives the weight training signal.

14. The system as claimed in claim 9, wherein free weight equipment comprises dumbbells, barbells, kettlebells, adjustable dumbbells, medicine balls, sandbells, weight plates, weighted bags, other types of free weights, or combinations thereof.

15. The system as claimed in claim 9, wherein when the signal receiver receives the weight training signal, the controller is operable to stop operation of the motor to stop rotation of the endless belt.

16. A method of verifying use of an exercise apparatus, comprising:
operating an operating member driven by a motor;
generating exercise use data in response to operation of the operating member;
transmitting the exercise use data by a controller to a communication interface while the operating member is driven by the motor; and
stopping transmitting the exercise use data to the communication interface if the exercise apparatus receives a weight training signal from free weight equipment, wherein the weight training signal is transmitted from the free weight equipment when the free weight equipment is in use.

17. The method as claimed in claim 16, wherein the operating member comprises an endless belt and the motor coupled to the endless belt for driving the endless belt to rotate; and wherein when the endless belt is driven by the motor without receiving the weight training signal, the controller determines that the user is engaging the endless belt and transmits the exercise use data; when the exercise apparatus receiving the weight training signal, the controller determines that the user is not engaging the endless belt and stops transmitting the exercise use data.

18. The method as claimed in claim 17, wherein when the exercise apparatus receives the weight training signal and the endless belt is continuously driven by the motor, the controller is programed to stop operation of the motor to stop rotation of the endless belt.

19. The method as claimed in claim 16, wherein the free weight equipment has a signal transmitter embedded therein, when the free weight equipment is operated by the user, the signal transmitter will transmit the weight training signal to the exercise apparatus.

20. The method as claimed in claim 16, wherein the controller is configured to generate validated exercise use data when the endless belt is driven by the motor and to generate non-validated exercise use data when the signal receiver receives the weight training signal.

\* \* \* \* \*